(12) United States Patent
Reid et al.

(10) Patent No.: US 6,869,926 B1
(45) Date of Patent: Mar. 22, 2005

(54) THERAPEUTIC METHOD

(75) Inventors: Ian Reginald Reid, Auckland (NZ); Jillian Cornish, Auckland (NZ)

(73) Assignee: Auckland UniServices Limited (AU)

( * ) Notice: Subject to any disclaimer, the term of this patent is extended or adjusted under 35 U.S.C. 154(b) by 0 days.

(21) Appl. No.: 09/509,306

(22) PCT Filed: Sep. 25, 1998

(86) PCT No.: PCT/NZ98/00145

§ 371 (c)(1), (2), (4) Date: Oct. 17, 2000

(87) PCT Pub. No.: WO99/16406

PCT Pub. Date: Apr. 8, 1999

(30) Foreign Application Priority Data

Sep. 26, 1997 (NZ) .............................................. 328853

(51) Int. Cl.[7] .............................................. A61K 38/16
(52) U.S. Cl. ........................... 514/2; 530/300; 424/93.7
(58) Field of Search ............................ 514/2; 530/300; 424/93.7

(56) References Cited

FOREIGN PATENT DOCUMENTS

| EP | 0 408 284 | | 5/1996 | .......... | A61K/38/00 |
|---|---|---|---|---|---|
| US | WO 9602269 | * | 2/1996 | .......... | A61K/38/17 |
| WO | 97/07214 | | 2/1997 | .......... | C12N/15/16 |
| WO | 97/38704 | | 10/1997 | .......... | A61K/38/00 |

OTHER PUBLICATIONS

Fisher, J. A. et al. (2002) Functional relevance of G-protein-coupled-receptor-associated proteins, exemplified by receptor-activity-modifying proteins (RAMPs). Biochem. Soc. Trans. vol. 30, pp. 455–460. Review.*

Christopoulos, G. et al. (1999) Multiple amylin receptors arise from receptor activity–modifying protein interaction with the calcitonin receptor gene product. Mol. Pharmacol. vol. 56, pp. 235–242.*

Cornish, J. et al. (1998) Dissociation of the effects of amylin on osteoblast proliferation and bone resorption. Am J Physiol. vol. 274, pp. E827–E833.*

Ng. M. C. Y. et al. (2001) Familial early–onset type 2 diabetes in Chinese patients: obesity and genetics have more significant roles than autoimmunity. Diabetes Care. vol. 24, pp. 663–671.*

Cornish et al., "Adrenomedullin is a Potent Simulator of Osteoblastic Activity In Vitro and In Vivo", American Journal of Physiology 273:E113–E1120, 1997.

Cornish et al., "Dissociation of the Effects of Amylin on Osteoblast Proliferation and Bone Resorption", American Journal of Physiology 274:E827–E833, 1998.

Cornish et al., "Systemic Administration of Amylin Increases Bone Mass, Linear Growth, and Adiposity in Adult Male Mice", American Journal of Physiology 275:E694–E699, 1998.

Reid et al, "Amylin and CGRP", Principles of Bone Biology pp 495–505, 1996.

* cited by examiner

*Primary Examiner*—Karen Cochrane Carlson
*Assistant Examiner*—Samuel Wei Liu
(74) *Attorney, Agent, or Firm*—Fish & Richardson P.C.

(57) ABSTRACT

The present invention relates to new therapeutic use of amylin as agent which stimulates chondrocyte proliferation and which therefore have utility in the treatment of cartilage disorders and/or cartilage mediated bone growth.

5 Claims, 3 Drawing Sheets

SEQUENCE LISTING

<160> NUMBER OF SEQ ID NOS: 3

<210> SEQ ID NO 1
<211> LENGTH: 37
<212> TYPE: PRT
<213> ORGANISM: Rattus norvegicus

<400> SEQUENCE: 1

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
             20                  25                  30

Gly Ser Asn Thr Tyr
         35

<210> SEQ ID NO 2
<211> LENGTH: 8
<212> TYPE: PRT
<213> ORGANISM: Rattus norvegicus

<400> SEQUENCE: 2

Lys Cys Asn Thr Ala Thr Cys Ala
 1               5

<210> SEQ ID NO 3
<211> LENGTH: 26
<212> TYPE: PRT
<213> ORGANISM: Homo sapiens

<400> SEQUENCE: 3

Ala His Gln Ile Tyr Gln Phe Thr Asp Lys Asp Lys Asp Asn Val Ala
 1               5                  10                  15

Pro Arg Ser Lys Ile Ser Pro Gln Gly Tyr
             20                  25

THERAPEUTIC METHOD

This application is a 371 of PCT/NZ98/00145 filed 25 Sep. 1998, which claims foreign priority benefit of the filing date under 35 U.S.C. 119 of New Zealand patent No. 328853, filed 29 Sep. 1998.

This invention is directed to new therapeutic uses which involve the stimulation of chondrocyte proliferation. More particularly, it is directed to the use of amylin and adrenomedullin as agents which stimulate chondrocyte proliferation and which therefore have utility in the treatment of cartilage disorders and/or cartilage mediated bone growth.

BACKGROUND

Amylin is a 37-amino acid peptide cosecreted with insulin from the beta cells of the pancreatic islets. It was first reported by Cooper et al in Proceedings of the National Academy of Sciences, USA 84, 8628 (1987) and is the subject of European Patent 289287. Amylin has the following peptide sequence:

```
                                            (SEQ ID NO:1)
Lys-Cys-Asn-Thr-Ala-Thr-Cys-Ala-Thr-Gln-
 1               5                   10

Arg-Leu-Ala-Asn-Phe-Leu-Val-His-Ser-Ser-
11              15                  20

Asn-Asn-Phe-Gly-Ala-Ile-Leu-Ser-Ser-Thr-
21              25                  30

Asn-Val-Gly-Ser-Asn-Thr-Tyr
31              35
```

The native molecule contains a disulphide bridge between the cysteine residues shown at positions 2 and 7 in the primary structure, is amidated at its COOH-terminus, and is formed as a propeptide.

European Patent 289287 reports a number of biological effects including enhancement of hepatic glucose output, increased production of lactate from skeletal muscle and reduced action of insulin in skeletal muscle.

Amylin is also reported in European Patent 408284 as having value for treatment of bone disorders and calcium imbalance. The patent specification attributes the activity of amylin to an inhibition of osteoclast motility. It is also resorted in WO 96/02269 as stimulating bone growth through stimulating osteoblas; proliferation.

Adrenomedullin is a 52-amino acid peptide first described in 1993 by Kitamura et at (Kitamura, K., et al. Adrenomedullin, a novel hypotensive peptide isolated from human pheochromocytoma. Biochem. Biophys. Res. Commun. 192:553–560 (1993)). It is present in normal adrenal/medulla and in many other tissues including the atria, ventricles, endothelial cells, lungs, brain, kidneys and bone.

Adrenomedullin shows approximately 20% sequence identity with amylin and can therefore be termed a related peptide (Muff, R., et al. Calcitonin, calcitonin gene-related peptide, adrenomedullin and amylin: homologous peptides, separate receptors and overlapping biological actions. Eur. J. Endocrinol. 133:17–20 (1995)). Both peptides have an NH$_2$ terminal ring created by a disulphide bond and are amidated at their COOH terminals.

Like amylin, adrenomedullin is also reported to have a range of activities. It is a potent vasodilator. It also has value in the treatment of bone disorders. This is primarily through an ability to stimulate osteoblast activity and proliferation in vitro and in vivo (Cornish, J., at al Adrenomedullin is a potent stimulator of osteoblastic activity in vitro and in vivo. Am. J. Physiol (Endocrinol Metab) 36:E1113–E1120, (1997)).

However, to date, there has been no report of either of the peptides amylin or adrenomedullin, as having any effect on chondrocytes. It is the applicants finding that both of these peptides are effective in the stimulation of chondrocyte proliferation and therefore on the growth of both cartilage and lineal bone. This effect is believed to be mediated through a single receptor on chondrocytes which underlies the applicant's invention.

SUMMARY OF THE INVENTION

The invention has a number of aspects. In a first aspect, the invention provides a method of treating a patient to stimulate chondrocyte proliferation in vivo which comprises the step of increasing the active concentration of amylin within said patient.

Another aspect provides a method of treating a patient to stimulate chondrocyte proliferation in vivo which comprises the step of administering to said patient amylin or an analog thereof in an amount effective to stimulate chondrocyte proliferation.

In another embodiment, the invention provides a method of treating a patient to stimulate chondrocyte proliferation in vivo which comprises the step of increasing the active concentration of adrenomedullin within said patient.

In a further embodiment, the invention provides a method of treating a patient to stimulate chondrocyte proliferation in vivo which comprises the step of administering to said patient adrenomedullin or an analog thereof in an amount effective to stimule chondrocyte proliferation.

In still a further aspect, the invention provides a method of treating a patient to stimulate chondrocyte proliferation in vivo which comprises the step of activating the receptor localised on chondrocytes of said patient to which amylin and/or adrenomedullin bind.

Most preferably, the method involves activation of the adrenomedullin receptor.

Conveniently, in each of the above methods the stimulation of chondrocyte proliferation is part of a method of treating a patient to stimulate cartilage growth and/or repair or to stimulate bone growth.

The invention also provides a method of stimulating chondrocyte proliferation in vitro which comprises administering an amount of amylin, adrenomedullin or an analog of either amylin or adrenomedullin to said chondrocytes which is effective in inducing chondrocyte proliferation.

Other aspects include:

the use of amylin or an analog thereof in the preparation of a medicament for effecting chondrocyte proliferation;

the use of adrenomedullin or an analog thereof in the preparation of a medicament for effecting chondrocyte proliferation;

the use of a ligand which binds to and activates the receptor to which amylin and/or adrenomedullin binds (preferably the adrenomedullin receptor) in the preparation of a medicament for effecting chondrocyte proliferation;

the use of an amylin agonist in the preparation of a medicament for effecting chondrocyte proliferation;

the use of an adrenomedullin agonist in the preparation of a medicament for effecting chondrocyte proliferation;

the use of amylin-(1–8) (SEQ ID NO:2) in the preparation of a medicament for effecting chondrocyte proliferation; and the use of adrenomedullin-(27–52) (SEQ ID NO:3) in the preparation of a medicament for effecting chondrocyte proliferation.

DESCRIPTION OF THE DRAWINGS

The present invention is broadly as defined above. However, it will be appreciated by those persons skilled in the art that it is not limited thereto and that it also includes embodiments which are more particularly described below and illustrated by the experimental data presented. This data includes the information shown in the accompanying drawings in which.

DESCRIPTION OF THE INVENTION

Figure 1:
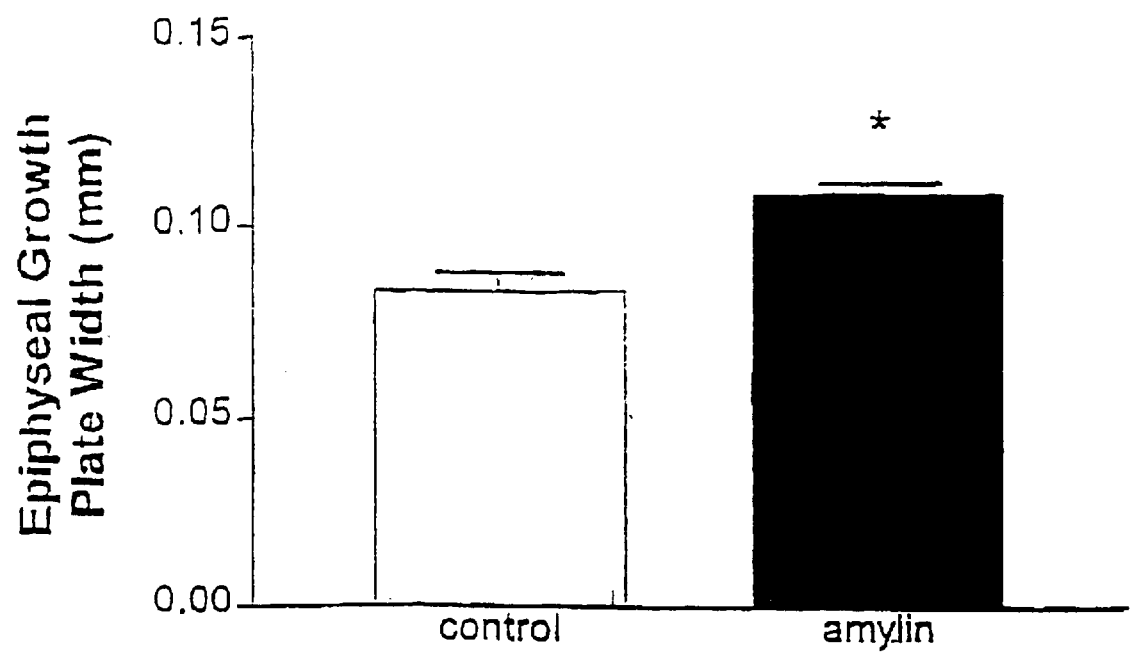
FIG. 1 shows the effects of daily systemic administration of amylin for 4 weeks on growth plate width in the tibiae of normal adult male mice. n=20 in each group. ★, significantly different from control, P=0.0002.

As broadly defined above, the present invention relates primarily to methods for stimulating chondrocyte proliferation. The invention therefore has utility in any application where stimulation of chondrocyte proliferation or growth is viewed as desirable, including for example cartilage growth and bone growth.

The applicants have found that chondrocyte proliferation is able to be effected using a number of related approaches. A first such approach is through a focus upon amylin. The applicants have found that increasing the effective concentration of amylin within a patient able to interact with the patients chondrocytes has the effect of stimulating chondrocyte proliferation.

Amylin for use in accordance with this approach can be obtained from any convenient commercial source (such as Bachem Calif., Torrence, Calif., USA). Alternatively, amylin can be synthesised, using the procedure as described by way of example in EP 408284.

The amylin used can be homologous or heterologous to the patient to be treated. For example, amylin from humans and other mammals eg. rat, monkey, dog, cat, mouse, guinea pig, hamster, degus, rabbit and hare can be used. The structure of these various peptides is reported in Endocrine Reviews 1994, 15(2) 163 by Garth J S Cooper which is incorporated herein by reference.

Most conveniently, the effective concentration of amylin will be increased through direct administration using either amylin itself or an amylin pro-drug (a form which is cleaved within the body to release amylin). It is however not the applicants intention to exclude increasing amylin concentration through administration of either amylin agonists (substances which effect a direct increase in the production or activity of amylin within the body, or inhibitors of amylin antagonists (substances which bind amylin or otherwise prevent or reduce the action of amylin within the body, These latter compounds exert an indirect effect on effective amylin concentrations through the removal of an inhibitory mechanism.

Another possibility is administration of a replicable vehicle encoding amylin to the patient. Such a vehicle (which may be a modified cell line or virus which expresses amylin within the patient) could have application in increasing the concentration of amylin within the patient for a prolonged period.

It is also contemplated that amylin analogs can be employed in this invention. As used herein "analog" means a protein which is a variant of another protein through insertion, deletion or substitution of one or more amino acids but which retains at least substantial functional equivalency.

A protein is a functional equivalent of another protein for a specific function if the equivalent protein is immunologically cross-reactive with, and has at least substantially the same function as, the original protein. The equivalent can be, for example, a fragment of the protein, a fusion of the protein with another protein or carrier, or a fusion of a fragment with additional amino acids. For example, it is possible to substitute amino acid in a sequence with equivalent amino acids using conventional techniques. Groups of amino acids normally held to be equivalent are:

(a) Ala, Ser, Thr, Pro, Gly;
(b) Asn, Asp, Glu, Gln;
(c) His, Arg, Lys;
(d) Met, Leu, Ile, Val; and
(e) Phe, Tyr, Trp.

In the case of amylin, the preferred analogs are fragments of the protein. In particular, amylin (1–8) can be used (ie. a fragment consisting of amino acids 1 to 8 of the amylin sequence).

Functional equivalency of analogs can also be readily screened for by reference to the ability of the analog to both bind to and activate the appropriate receptor.

In addition to the above approach, which focuses upon amylin and its analogs, the invention provides a further approach to chondrocyte proliferation. This second approach has a focus upon adrenomedullin. The applicants have found that, in an equivalent manner to amylin, increasing the effective concentration of adrenomedullin within a patient able to interact with the chondrocytes in that patient stimulates chondrocyte proliferation.

For use in this approach, adrenomedullin can be obtained from any convenient commercial source or, as is the case with amylin, synthesised using techniques well known in the art. Such techniques include those described hereinafter.

Again, it is most convenient that the effective concentration of adrenomedullin be increased through direct administration using either adrenomedullin itself or an adrenomedullin pro-drug. However, adrenomedullin agonists or inhibitors of adrenomedullin antagonists are not excluded.

As with amylin, adrenomedullin can also be administered in the form of a replicable vehicle encoding adrenomedullin to the patient for release of adrenomedullin over a prolonged period.

Adrenomedullin analogs can also be employed. For this purpose, the term "analog" has the equivalent meaning of that given above for amylin. In the case of adrenomedullin, a particularly preferred analog is adrenomedullin (27–52) (ie. a fragment consisting of amino acids 27–52 of the adrenomedullin sequence).

The invention still further provides a third approach to chondrocyte proliferation. This further approach focuses upon the receptors on chondrocytes to which amylin and adrenomedullin bind and upon effecting chondrocyte proliferation through use of any ligand which both binds to and activates these receptors.

It will be appreciated that amylin analogs of amylin, adrenomedullin and analogs of adrenomedullin are all ligands which achieve this. Indeed, the use of these substances as active agents represents a preferred aspect of the invention. However, it should be appreciated that this approach has not restricted the use or amylin, adrenomedullin and their analogs but also extends to any ligand which fulfils the functional requirement of both binding to and activating (stimulating) the amylin or adrenomedullin receptors. Such additional ligands are, for example, believed to include peptides such as calcitonin gene related peptide (Muff, R., et al. Calcitonin, calcitonin gene-related peptide, adrenomedullin and amylin: homologous peptides, separate receptors and overlapping biological actions. Eur. J. Endocrinol 133:17–20 (1995)).

A specific feature of this approach is to employ ligands which bind to and activate the adrenomedullin receptor. This receptor was described in, for example, Kapas, S., et al. Cloning and expression of cDNA encoding a rat adrenomedullin receptor. J. Biol. Chem. 270:25344–25347 (1995). It is further described in Montuenga, L. M., et al. Expression of adrenomedullin and its receptor during embryogenesis suggests autocrine or paracrine modes of action. Endocrinology 138:440–451 (1997)).

Additional stimulatory ligands can therefore, for example, be identified by a screening protocol employing at least the ligand binding domain of the adrenomedullin receptor. This screening method can, for example, utilise the expression of the adrenomedullin receptor in Xenopus oocytes using standard recombinant DNA methods and measurement of the adrenomedullin receptor-mediated signal transduction evoked by novel stimulatory ligands.

For therapeutic application, the active compound (amylin, adrenomedullin analog or ligand) will be formulated as a medicament. The details of the formulation will ultimately depend upon the active compound itself and upon the route of administration chosen. It will however be usual for the medicament to include combination of the active compound with a suitable carrier, vehicle or diluent.

Dosage rates will also be active compound and administration route dependent. However, by way of example, the dosage of active compound to be administered by injection will be in the range of 0.01–100 mg/kg of body weight Further, while formulations in which the active compounds represent the sole active principle are most likely to be used, it is by no means intended that formulations which are suitable for combination therapies be excluded. The active compound can be administered together with any other therapeutic agent, including any other agent which has an effect on chondrocyte proliferation.

The invention, in its various aspects, will now be illustrated by the experimental section which follows. It will however be appreciated that the experiments are non-limiting.

Experimental
Methods
(a) Chondrocyte Monolayer Cell Cultures

Fresh cartilage samples were collected from the tibial plateaus and femoral condyles of mature, healthy crossbred dogs 12–4 years, 20–25). The chondrocytes were isolated as previously described (Connective Tissue Research 1988; 18:205–222). Briefly, the chondrocytes were obtained by pronase and collagenase digestion of the cartilage, then the cells were centrifuged, washed and resuspended in media before being cultured in 75 cm$^2$ tissue culture flasks. The cells were incubated under 5% $CO_2$ and 95% air at 37° C. Confluence was reached by 7–10 days, at which time the cells were subcultured. After trypsinization, the cells are rinsed and resuspended in fresh medium, then seeded at $5\times10^4$ cells/ml in 24-well plates (0.5 ml cell suspension per well, ie. $1.4\times10^4$ cells/cm$^2$). Proliferation studies (cell counts and thymidine incorporation) were performed. Subconfluent population were changed to serum-free medium with 0.1% bovine serum albumin plus the experimental compounds. Cell numbers were analysed at 24 hours after addition of the peptide or vehicle. The cell numbers were determined using a haemocytometer chamber. Results were expressed per well. [$^3$H]-thymidine incorporation was assessed by pulsing the cells with [$^3$H]-thymidine (luCi/well) two hours before the end of the experimental incubation. The experiment was terminated at 24 hours by washing the cells in media containing cold thymidine followed by the addition of 10% tricholoroacetic acid. The precipitate was washed twice with ethanol ether (3:1) and the wells desiccated at room temperature. The residue was redissolved in 2 M KOH at 55° C. for 30 mins, neutralised with 1 M HCl, and an aliquot counted for radioactivity. Results were expressed as dpm per well. For both cell counts and thymidine incorporation, each experiment was performed at least 4 different times using experimental groups consisting of at least 6 wells.

(b) Chondrocytes 3-Dimensional Cell Cultures In Alginate Beads Alginate head cultures were established as described by Guo, et al. Culture and growth characteristics of chondrocytes encapsulated in alginated beads. Connective Tissue Research 19:277–297 (1989). Briefly the cells were suspended in a solution of 1.25%/wt/vol) alginate in HEPES (20 mM HEPES buffer pH neutral) at a density of $2\times10^6$ cells/ml> The suspension of chondrocytes were slowly extruded through a 22-gauge needle in a dropwise manner into 40 ml of 0.1 M $CaCl_2$ solution. After instantaneous gelation, the beads were allowed to further polymerise in $CaCl_{/2}$ solution (10 mins, room temperature). The beads were washed sequentially, twice in 0.15 M NaCl and twice in Dulbecco's modified Eagle's medium (DME). After the washing procedure, the beads were placed into 24-well culture plates (10 beads/well) and fed with 1 ml 10% fetal calf serum (FCS) SMW with 5 µg/ml ascorbic acid. The cultures were maintained at 37° C. in a humidified atmosphere of 5% $CO_2$ in air. The medium was changed every second day. On day 4 and 6 of culture, peptide or vehicle was added. Cell numbers were analysed at day 8 by exposing alginate beads to 50 mM ethylenediaminetetraacetic acid (EDTA) for approximately 10 minutes at 37° C. Counting was performed in a haemocytometer chamber. Results were expressed per well. Tritiated-thymidine incorporation ($^3$H-thymidine) was assessed by pulsing the beads with $^3$H-thymidine (1 µCi/well) 48 hours before the end of experimental incubation. Experiments were then terminated at day 8 of culture by dissolving the beads in 50 mM EDTA. The cells were washed twice with distilled water by centrifuging. Pellets were resuspended and counted for radioactivity.

(c) In Vivo Study: Experimental Design

Two groups of 20 sexually mature male Swiss mice aged between 40 and 50 days and weighing 25–32 g, were given daily subcutaneous injections (50 ul) in the loose skin at the nape of the neck for 5 days/week over 4 consecutive weeks. The treated group was injected with peptide at a dose of 300 ug/kg/injection and the control group was injected with vehicle (water). Animals were housed in a room maintained at 20° C. on 12-hour light/dark cycles. They were fed diet 86 rodent pellets (New Zealand Stockfeed Ltd) ad libitum throughout the experiment. Each animal's weight was recorded at the beginning and end of the experiment One day after the last injection, animals were sacrificed by cervical dislocation. They study had the approval of the local institutional review board.

The tibiae were dissected free of adherent tissue. Tibial lengths were recorded by measuring the distance between the proximal epiphysis and the distal tibio-fibular junction using an electronic micrometer Digimatic Calipers, Mitutoyo, Japan). Bones were placed in 10% phosphate-buffered formalin for 24 hours and then dehydrated in a graded series of ethanol solutions and embedded, undecalcified, in methylmethacrylate resin. Tibiae were sectioned longitudinally through the frontal plane and calvariae were cut cross-sectionally at the base of the parietal bone. All sections were 4 um think and were cut on a Leitz microtome using a tungsten-carbide knife (Microknife Sharpening, Utah, USA). Sections were mounted on gelatincoated slides and air-dried. They were stained with Goldner's tri-chrome and examined using an Olympus BX 50 microscope (Olympus Optical Co Ltd, Tokyo, Japan) which was attached to an Osteomeasure Image Analyzer (Osteometrics Inc. Atlanta, Ga.).

Tibial histomorphometric analyses were made from three adjacent sections one third of the way through the anterior/posterior depth of the proximal tibiae. Epiphyseal growth plate thickness was measured at three sites evenly spaced along its length. All measurements were made by one operator who was blinded to the treatment group of each bone.

Materials

Rat amylin was sourced from Bachem Calif., Torrance, Calif., USA. Lyophilised material was dissolved in water prior to administration. Methylmethacrylate was purchased from Acros Organics N.V., Geel, Belgium.

Rat amylin-(1–8) used in this study was a COOH-terminal amide synthesized on methylbenzhydrylamine resin by standard solid-phase techniques followed by hydrogen fluoride deprotection and cleavage from the resin. Amylin-(1–8) was cyclized in a dilute solution of 90% acetic acid by treatment with methanol solutions of iodine and punned to >96% homogeneity by reverse-phase high performance liquid chromatograph (RP HPLC). Structures were confirmed by matrix-assisted laser desorption ionization time-of-flight mass spectrometry (MALDI-TOF system, model G2025 A, Hewlett Packard CA, USA) and amino acid analysis of acid hydrolysates %%4929%%.

Human adrenomedullin and its fragments were synthesized on methylbenzhydxylamine resin using standard solid-phase procedures, and cleaved with hydrogen fluoride/anisole. Sequences containing a disulfide bridge were cyclized by titration with $1_2$ in 90% acetic acid/water solutions. Crude materials were purified by gel filtration on Sephadex columns in 50% acetic acid followed by gradient elution on C18 silica using acetonitrile/0.1% trifluoroacetic acid eluants. Homogeneity of final peptides was assessed by thin layer chromatography, analytical HPLC, amino acid analysis and matrix-assisted laser-desorption-ionization mass spectroscopy. Purities were usually >98%.

Statistical Analysis

Data are presented as mean±sem. Where parameters have been measured more than once in each animal these values have been averaged to produce a single value for each animal before further analysis. The significant of treatment effects was evaluated using Student's t tests for unpaired data. These comparisons were specified a priori, so adjustment of $\alpha(0.05)$ was not necessary.

Results

Amylin (a) Chondrocyte Cell Cultures

Amylin influenced chondrocyte proliferation, increasing cell numbers from 4.12±0.23 ($\times10^4$) (mean±sem) in control cells to 5.11±0.21 ($\times10^4$) in those cells incubated with amylin (p=0.01) as well as increasing thymidine incorporation (ie. DNA synthesis) from 20725±997 dpm in control cells to 25937±1203 dpm in amylin-treated cells.

(b) Chondrocytes 3-Dimensional Cell Cultures In Alginate Beads

Amylin again influenced chondrocyte proliferation, increasing cell numbers from 5.58±0.16 ($\times10^4$) (mean±sem) in control cells to 6.07±0.05 ($\times10^4$) in those cells incubated with amylin ($10^{-10}$M) (p<0.03) as well as increasing thymidine incorporation (ie. DNA synthesis) from 1135±85 dpm in control cells to 2584=229 dpm in amylin-treated cells (p<0.01).

(c) In Vivo Study

Figure 2:
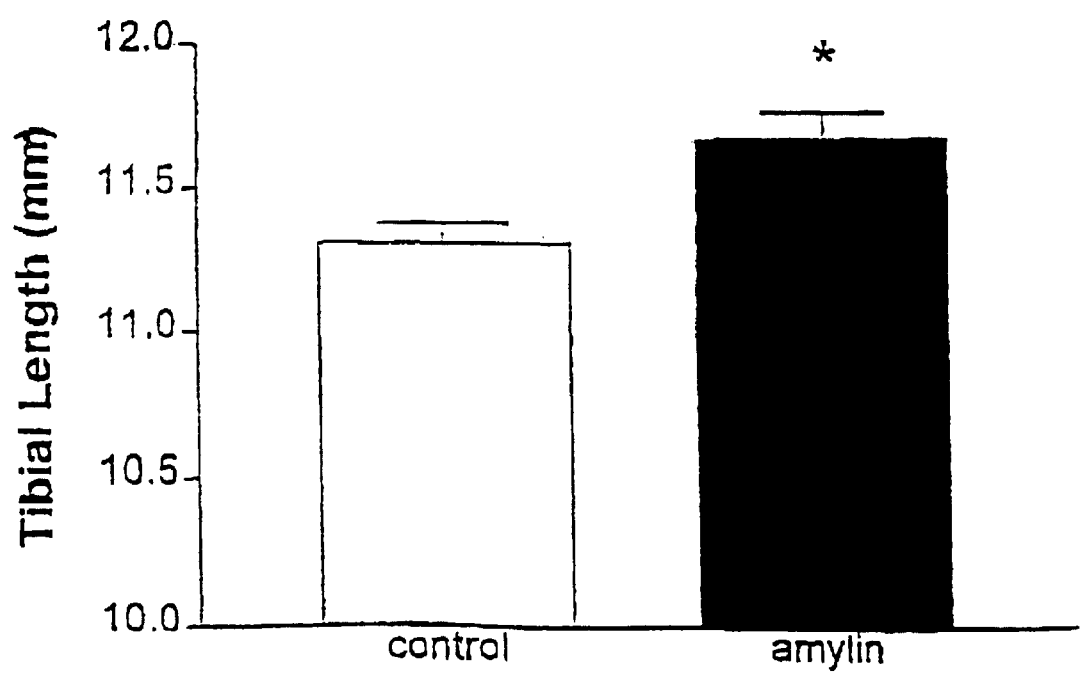
FIG. 2 shows the effects of daily systemic administration of amylin for 4 weeks on bone length in the tibiae of normal adult male mice. n=20 in each group. ★, significantly different from control, P=0.004.

Amylin influenced the tibial growth plate, increasing its width from 0.083±0.005 mm (mean±sem) in the control animals to 0.108±0.003 mm in those receiving amylin (P=0.0002) (FIG. 1). The total length of the tibiae was also increased from 11.31±0.07 mm in control animals to 11.67±0.09 mm in animals injected with amylin (P-0.004) (FIG. 2).

Amylin 1–8

(a) Amylin-(1–8) also influenced chondrocyte proliferation, increasing cell numbers from 3.23±0.11 ($\times10^4$) (mean±sem) in control cells to 3.63±0.09 ($\times10^4$) in those cells incubated with amylin-(1–8) (10–8M) (p=0.02) as well as increasing thymidine incorporation (DNA synthesis) from 26859±423 dpm in control cells to 28932±628 dpm in amylin-(1–8) treated cells (p=0.02).

Figure 3:
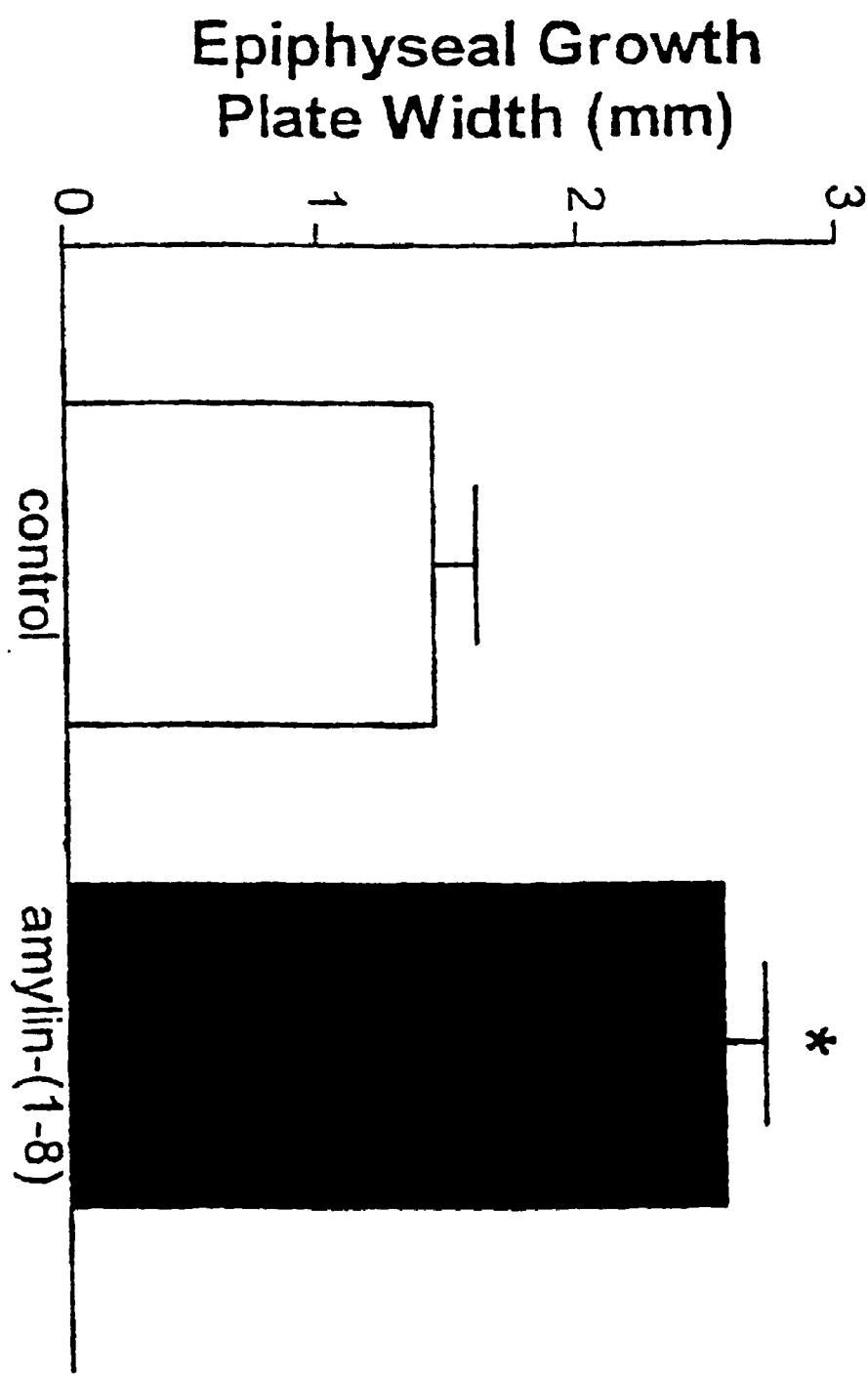
FIG. 3 shows the effect of the amylin fragment (amylin (1–8)) on epiphyseal growth plate width.

(c) The growth plate width in the proximal tibiae of mice injected systemically with amylin-(1–8) is significantly increased compared to control animals (mean±sem: 0.111 mm±0.004 compared to 0.081 mm±0.004; p<0.000 I). See FIG. 3.

Adrenomedullin (a) Adrenomedullin influenced chondrocyte proliferation, increasing cell numbers from 1.79±0.07 ($\times10^4$) (mean±sem) in control cells to 2.27±0.12 ($\times10^4$) in those cells incubated with adrenomedullin ($10^{-9}$M) (p<0.01).

Adrenomedullin-(27–52)

Figure 4:
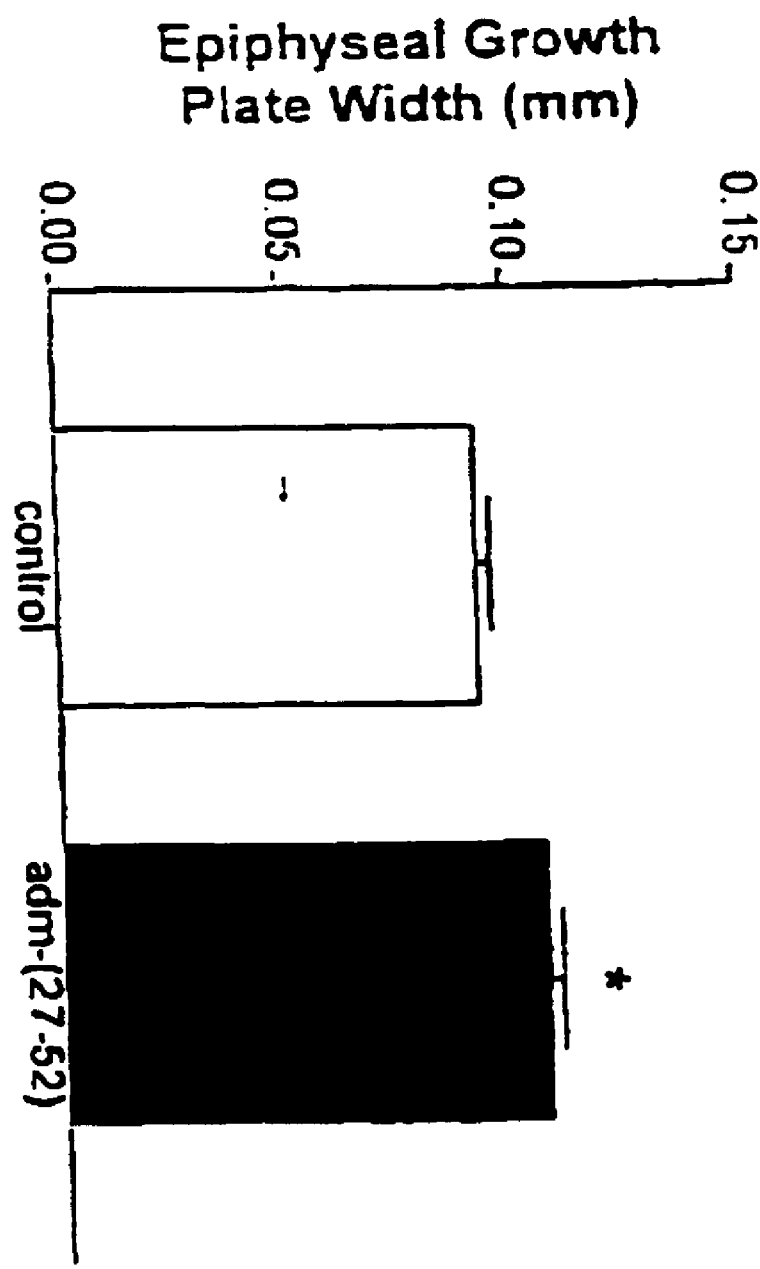
FIG. 4 shows the effect of the adrenomedullin fragment (adm 27–52) on epiphyseal growth plate width.

(c) Adrenomedullin-(27–52) increased the growth plate width from 0.094 mm±0.003 (mean±sem) in control animals to 0.11 mm±0.003 in adrenomedullin-(27–52) (p=0.003). See FIG. 4.

Industrial Application

The above results clearly show that amylin and its anlogs (amylin-(1–8) for example) has the ability to stimulate chondrocyte proliferation. Similarly, adrenomedullin and its analogs (adrenomedullin-(27–52) have equivalent capability.

The results additionally show the ability of both amylin, adrenomedullin and their analogs to influence the growth of cartilage as well as increased bone growth. This latter effect is consistent with the formation of bone on a template of cartilage tissue.

Both amylin and adrenomedullin are believed to be exerting the effect on chondrocyte proliferation/cartilage growth/bone formation through the mediation of the amylin/adrenomedullin receptor.

The present invention therefore provides new approaches to chondrocyte proliferation. These involve firstly increasing the active concentration of amylin/adrenomedullin in a patient and secondly the activation of the amylin/adrenomedullin receptor localised on chondrocyte cells.

The approaches of the invention have application in the treatment of patients in a variety of conditions. Principal amongst these are conditions where the patient is suffering from a cartilage defect, either through injury or through degenerative, inflammatory or other disease.

The approaches of the invention also have application in the stimulation of bone growth, particularly lineal bone growth. This provides the invention with application in treating patients (for example, children) who are of short stature or who otherwise suffer from defects which would benefit from stimulation of the growth of limb bones.

The invention also has application in vitro. Extracted chondrocytes can be proliferated using the present methods. The proliferated chondrocytes can then be employed in methods of therapy, particularly those which involve the treatment of damaged cartilage.

It will be appreciated by those persons skilled in the art that the above description is provided by way of example only and that numerous changes and variations can be made while still being within the scope of the invention as defined by the appended claims.

What is claimed is:

1. A method of treating a patient to stimulate chondrocyte proliferation in vivo which comprises the step of increasing amylin activity within said patient by an amount effective to stimulate chondrocyte proliferation.

2. A method of treating a patient to stimulate cartilage growth or repair in vivo through stimulation of chondrocyte proliferation which comprises the step of increasing amylin activity within said patient by an amount effective to stimulate chondrocyte proliferation.

3. A method of treating a patient to stimulate chondrocyte proliferation in vivo which comprises the step of administering to said patient amylin or an analog thereof in an amount effective to stimulate chondrocyte proliferation, the amylin analog being a fragment of amylin comprising amylin (1–8) (SEQ ID NO:2).

4. A method of treating a patient to stimulate cartilage growth or repair in vivo through stimulation of chondrocyte proliferation which comprises the step of administering to said patient amylin or an analog thereof in an amount effective to stimulate chondrocyte proliferation, the amylin analog being, a fragment of amylin comprising amylin (1–8) (SEQ ID NO:2).

5. A method of stimulating chondrocyte proliferation in vitro which comprises administering an amount of amylin or an analog of amylin to said chondrocytes is in an amount effective in inducing chondrocyte proliferation, the amylin being a fragment of amylin comprising amylin (1–8).

* * * * *